US009613253B2

(12) United States Patent
Ly et al.

(10) Patent No.: US 9,613,253 B2
(45) Date of Patent: Apr. 4, 2017

(54) PORE-SPACE MEASUREMENT METHOD APPARATUS AND SYSTEM

(71) Applicant: CGG Services SA, Massy (FR)

(72) Inventors: Chi Vinh Ly, Katy, TX (US); Graham Spence, Llandudno (GB)

(73) Assignee: CGG SERVICES SAS, Massy (FR)

( * ) Notice: Subject to any disclaimer, the term of this patent is extended or adjusted under 35 U.S.C. 154(b) by 578 days.

(21) Appl. No.: 14/156,719

(22) Filed: Jan. 16, 2014

(65) Prior Publication Data
US 2015/0000903 A1  Jan. 1, 2015

Related U.S. Application Data

(60) Provisional application No. 61/839,932, filed on Jun. 27, 2013.

(51) Int. Cl.
| | | |
|---|---|---|
| *G06K 9/00* | (2006.01) | |
| *E21B 47/00* | (2012.01) | |
| *G01N 33/24* | (2006.01) | |
| *G01V 1/40* | (2006.01) | |

(52) U.S. Cl.
CPC .......... *G06K 9/00127* (2013.01); *E21B 47/00* (2013.01); *G01N 33/241* (2013.01); *G06K 9/0014* (2013.01)

(58) Field of Classification Search
USPC ........ 382/100, 103, 106, 108–111, 123, 140, 382/148, 162, 165, 168, 173, 181, 382/190–194, 199, 209, 219–220, 232, 382/254, 274–276, 286–291, 305, 312, 382/321, 172; 702/13; 703/1; 348/46; 175/17; 75/343
See application file for complete search history.

(56) References Cited

U.S. PATENT DOCUMENTS

| | | | | |
|---|---|---|---|---|
| 4,868,883 A | * | 9/1989 | Chen ................. | G06K 9/00127 382/109 |
| 2005/0087037 A1 | * | 4/2005 | Abercrombie ............ | C22B 1/00 75/343 |
| 2011/0004448 A1 | * | 1/2011 | Hurley .................... | G06T 17/00 703/1 |
| 2011/0181701 A1 | * | 7/2011 | Varslot .................. | G06T 7/0024 348/46 |

(Continued)

OTHER PUBLICATIONS

Jarvie, Daniel M. et al., Unconventional Shale-Gas Systems: The Mississippian Barnett Shale of North-Central Texas as One Model for Thermogenic Shale-Gas Assessment, AAPG Bulletin, vol. 91, No. 4, Apr. 2007, pp. 475-499.

*Primary Examiner* — Seyed Azarian
(74) *Attorney, Agent, or Firm* — Patent Portfolio Builders PLLC

(57) ABSTRACT

A method for determining pore-space metrics for geological samples may include receiving an image of a geological sample, determining, via image processing, pore-space regions within the image of the geological sample, and measuring the pore-space regions to provide a pore-space metric for the geological sample. The method may also include determining a geo-mechanical property for the geological sample using the pore-space metric and adjusting a hydrocarbon recovery operation according to the pore-space metric or the geo-mechanical property. A corresponding system and apparatus are also disclosed herein.

19 Claims, 10 Drawing Sheets

(56) References Cited

U.S. PATENT DOCUMENTS

2011/0222370 A1     9/2011  Downton et al.
2012/0316789 A1 * 12/2012  Suarez-Rivera ......... G01V 9/00
                                                                702/13
2013/0264118 A1 * 10/2013  Wideman .................. E21B 7/14
                                                                175/17

* cited by examiner

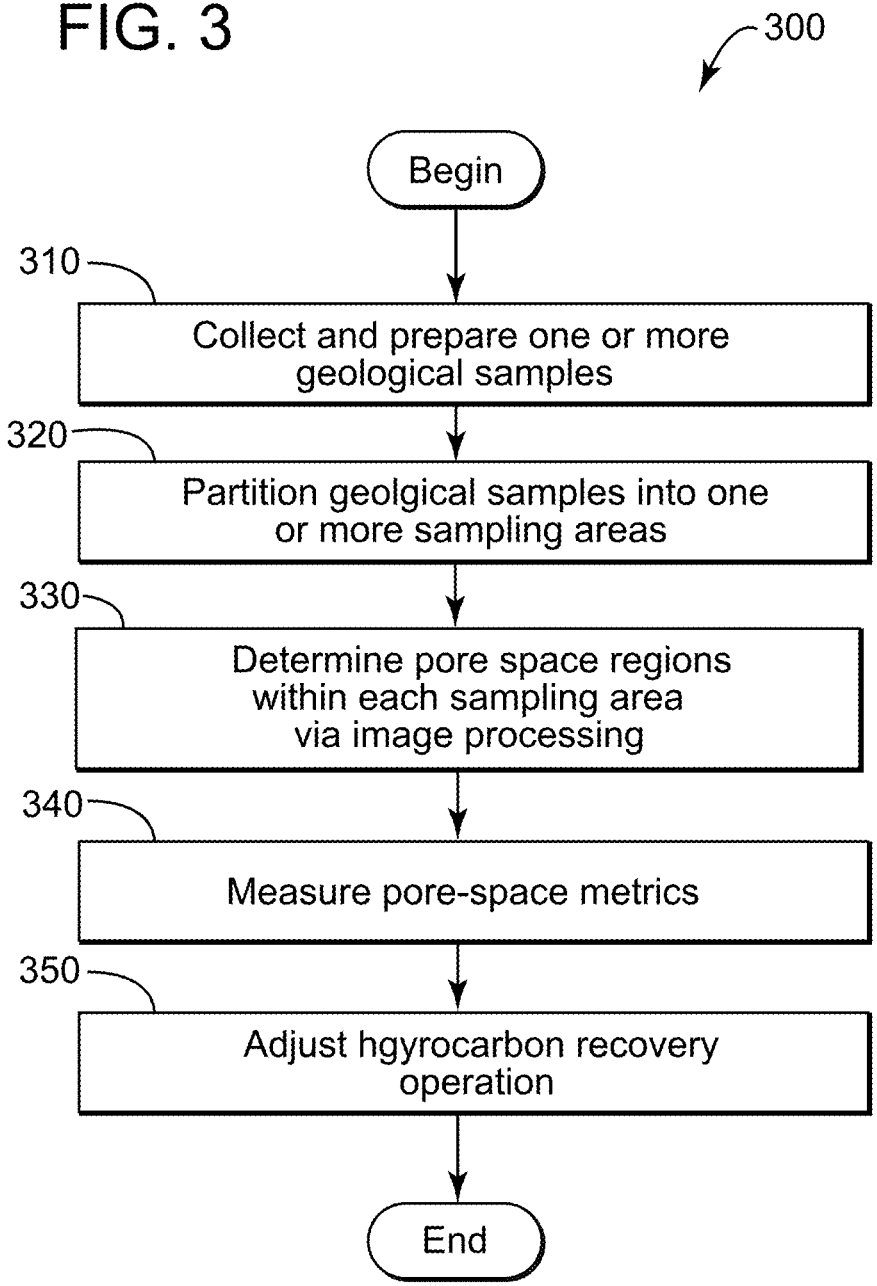

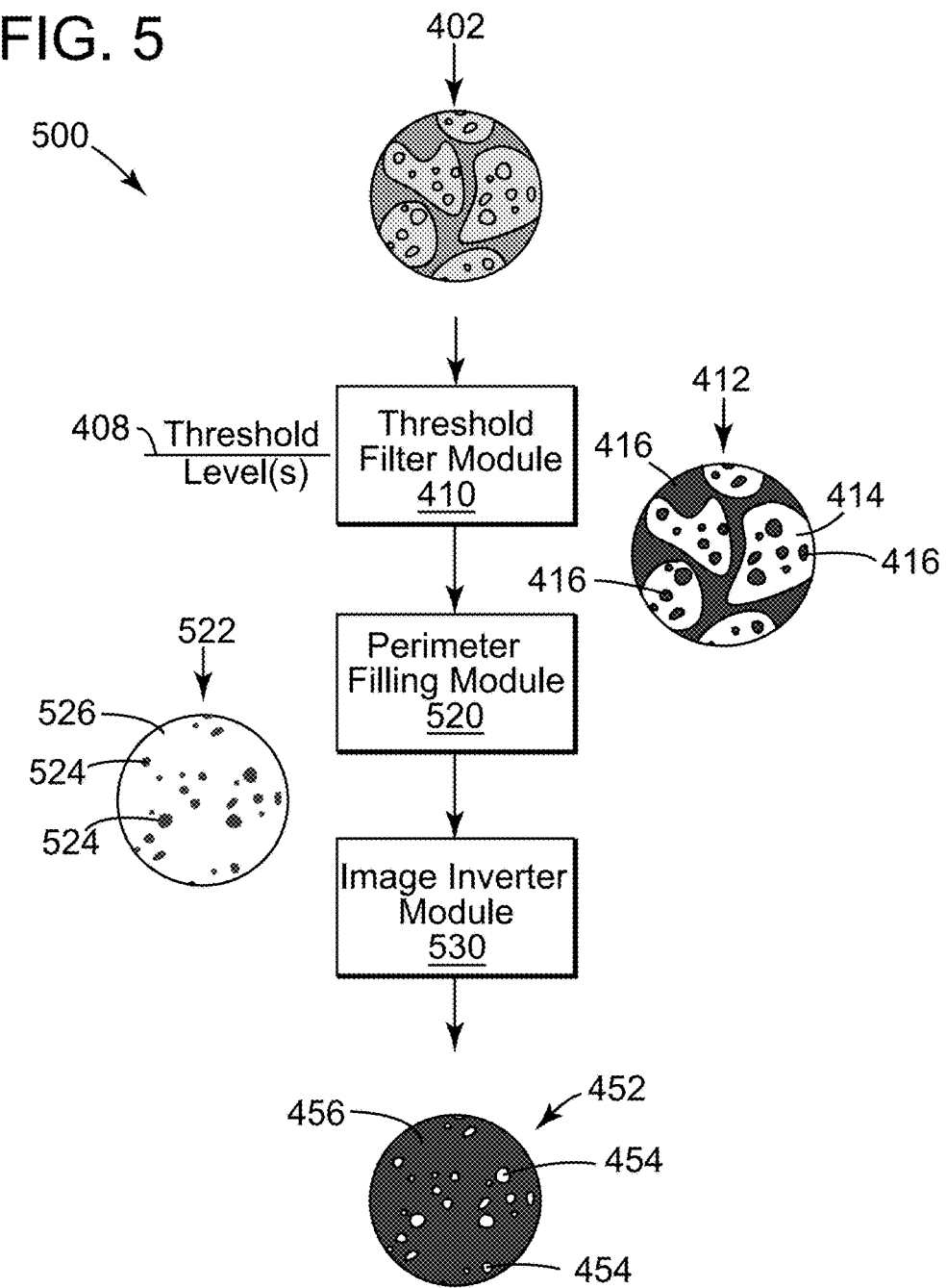

FIG. 6a

| ID | Area μm² | Feret Max Diameter μm | Feret Min Diameter μm |
|---|---|---|---|
| 2008801 | 0.92 | 096 | 0.96 |
| 2008800 | 6.45 | 3.99 | 1.92 |
| 2008798 | 4.6 | 3.1 | 1.92 |
| 2008797 | 11.97 | 6.13 | 2.84 |
| 2008796 | 10.13 | 4.42 | 2.88 |
| 2008795 | 12.89 | 5.25 | 2.88 |
| 2008794 | 12.89 | 5.76 | 3.62 |
| 2008793 | 25.78 | 8.45 | 5.03 |
| 2008792 | 0.92 | 0.96 | 0.96 |
| 2008791 | 17.5 | 6.8 | 3.84 |
| 2008790 | 15.65 | 5.76 | 3.84 |
| 2008788 | 9.21 | 3.99 | 2.88 |
| 2008787 | 4.6 | 3.1 | 1.92 |
| 2008786 | 13.81 | 7.03 | 3.03 |
| 2008785 | 1.84 | 1.92 | 0.96 |
| 2008784 | 7.37 | 3.67 | 2.88 |
| 2008783 | 8.29 | 3.67 | 2.88 |
| 2008782 | 11.05 | 5.25 | 2.88 |
| 2008781 | 8.29 | 4.42 | 2.8 |
| 2008778 | 36.84 | 15.48 | 3.84 |
| 2008777 | 4.6 | 3.1 | 1.92 |
| 2008776 | 23.02 | 8.45 | 4.95 |
| 2008775 | 11.97 | 4.42 | 3.84 |
| 2008774 | 12.89 | 5.85 | 2.88 |

PORE-SPACE MEASUREMENT METHOD APPARATUS AND SYSTEM

CROSS-REFERENCE TO RELATED APPLICATIONS

The present application is related to, and claims the benefit of priority of, U.S. Provisional Application 61/839, 932, entitled "A NEW METHOD FOR MEASUREMENT AND PROCESSING OF SEM IMAGES TO GENERATE PRIMARY AND SECONDARY PORE CHARACTERISTICS," and filed on 27 Jun. 2013, the entire content of which is incorporated herein by reference.

BACKGROUND

Technical Field

Embodiments of the subject matter disclosed herein generally relate to the field of hydrocarbon prospecting and extraction. In particular, the embodiments disclosed herein relate to apparatuses, methods, and systems for measuring the geo-mechanical properties of rock and adjusting hydrocarbon recovery operations in response to those measurements.

Discussion of the Background

Geophysical data is useful for a variety of applications such as weather and climate forecasting, environmental monitoring, agriculture, mining, and seismology. As the economic benefits of such data have been proven, and additional applications for geophysical data have been discovered and developed, the demand for localized, high-resolution, and cost-effective geophysical data has greatly increased. This trend is expected to continue.

For example, seismic data acquisition and processing may be used to generate a profile (image) of the geophysical structure under the ground (either on land or seabed) that facilitates finding and extracting hydrocarbon reserves. While this profile does not provide an exact location for oil and gas reservoirs, it suggests, to those trained in the field, the presence or absence of such reservoirs.

Traditionally, a land seismic survey system 10 capable of providing a high-resolution image of the subsurface of the earth is generally configured as illustrated in FIG. 1 (although many other configurations are used). System 10 includes plural receivers 12 and acquisition units 12a positioned over an area 13 of a subsurface to be explored and in contact with the surface 14 of the ground. A number of seismic sources 16 are also placed on surface 14 in an area 17, in a vicinity of area 13 of receivers 12. A recording device 18 is connected to a plurality of receivers 12 and placed, for example, in a station-truck 20. Each source 16 may be composed of a variable number of vibrators or explosive devices, and may include a local controller 22. A central controller 24 may be present to coordinate the shooting times of the sources 16. A positioning system 26 (e.g. GPS, GLONASS, Galileo, and Beidou) may be used to time-correlate sources 16 and receivers 12 and/or acquisition units 12a.

With this configuration, the sources 16 are controlled to generate seismic waves, and the receivers 12 record the waves reflected by the subsurface. The receivers 12 and acquisition units 12a may be connected to each other and the recording devices with cables 30. Alternatively, the receivers 12 and acquisition units 12a can be paired as autonomous nodes that do not need the cables 30.

The purpose of seismic imaging is to generate high-resolution images of the subsurface from acoustic reflection measurements made by the receivers 12. Conventionally, as shown in FIG. 1, the plurality of seismic sources and receivers is distributed on the ground surface at a distance from each other. The sources 16 are activated to produce seismic waves that travel through the subsoil. These seismic waves undergo deviations as they propagate. They are refracted, reflected, and diffracted at the geological interfaces of the subsoil. Certain waves that have traveled through the subsoil are detected by the seismic receivers 12 and are recorded as a function of time in the form of signals (called traces).

Once a promising region for hydrocarbon reserves is found, vertical and horizontal wells may be drilled to potentially extract the reserves. For example, in the United States and other regions of the world, there are many areas where oil shale rock deposits are to be found. Oil shale is a form of sedimentary deposits that were laid down eons ago, typically in the form of calcium carbonates, sodium carbonates, calcium bicarbonates, and quartz. Furthermore, soil materials and other compounds may have been entrapped in the matrix of the aforementioned materials.

While many oil shale reserves exist, most of them are located as deep deposits five to ten thousand feet below the surface of the earth. Since the early $20^{th}$ century, many attempts have been made to mine or extract the oil from stratified shale formations. Although historically the shale oil proved to be a very suitable hydrocarbon product, the complexity of extracting oil shale reserves increased the cost of production well beyond the market price of similar products. Consequently, sustained shale production proved to be uneconomical.

Recently, the rapid development and exploitation of two specialized technologies has dramatically changed the cost of extracting oil from shale rock deposits. The first improvement is the carefully controlled and steerable directional drilling techniques that enable vertical drilling to be redirected into horizontal drilling at a selected depth. The drilling can then continue horizontally in a shale formation for a considerable distance.

The second improvement was the development of hydraulic fracturing techniques where slurry is pumped into a well at regular perforation points along an inserted casing in order to extend the economic life of the depleting oil fields. Although first used in the late 1940's, hydraulic fracturing has recently become a common technique to enhance the production of low-permeability formations, especially unconventional reservoirs—primarily tight sands, coal beds, and deep shales.

Despite many improvements, the cost of fracturing is still relatively high and significant inefficiencies remain. For example, many oil shale formations cross tectonic fault lines in the crust of the earth and thus can be discontinuous in their configuration. Some oil shale formations are slightly inclined in both the vertical and horizontal planes. Consequently, the abundance of oil may vary significantly as a function of drilling distance. In fact, it is estimated that approximately 30 percent of the perforation points in a typical fracturing operation correspond to dry regions where oil is unavailable.

Referring to FIG. 2a, in horizontal shale gas wells, fracturing is typically done in multiple stages at regular fixed intervals starting at the "toe" of the well (the name given to the tip of the foot-shaped horizontal wellbore) and proceeding toward the "heel" (the end of the horizontal section of the wellbore that is closest to the vertical portion). For example, a wellbore that extends 5,000 feet laterally within a shale layer might be hydraulically fractured in ten to fifteen stages several hundred feet apart. Typically, each perforation interval is isolated in sequence so that only a single section of the well is hydraulically fractured at a given time and to prevent damage to other sections of the wellbore.

During a hydraulic fracturing operation, fracturing fluid is pumped at high pressure through perforations in the section of the casing. The chemical composition of the fracturing fluid, as well as the rate and pressure at which it is pumped into the shale formation, are tailored to the specific properties of each shale and, to some extent, each well. When the pressure increases to a sufficient level, a planar hydraulic fracture opens in the rock, propagating more or less perpendicularly to the path of the wellbore. Although the fractures depicted in FIG. 2a are by necessity shown to be substantially vertical, the casing perforations in a well are typically oriented to produce fractures that propagate horizontally rather than vertically.

It should be noted that the fracturing characteristics of shale rock may vary significantly between wells or even within the same well. For example, soft oil shale formations respond differently than hard oil shale formations when subjected to the same level of hydraulic water pressure and soaking time. In addition to the mineral composition, the fracturing characteristics of shale formations may be dependent on the texture or fabric of the shale rock. For example, shale formations with larger and/or more abundant pores may fracture more easily than shale formations with smaller and less abundant pores.

Referring to FIG. 2b, a typical hydro-fracture may propagate horizontally about 500-800 feet away from the well in each direction. The fracturing pressure is carefully controlled to prevent vertical propagation beyond the thickness of the layer of gas-producing shale. The pressure needed to propagate the hydraulic fracture varies and depends on depth, the pressure of the gas in the pores of the shale, and the geo-mechanical properties of the hydrocarbon bearing layer, such as porosity. Consequently, reliable and readily available measurements of the geo-mechanical properties of the hydrocarbon bearing layer, as well as adjacent layers, can improve the effectiveness of hydrocarbon recovery operations.

A variety of techniques exist for measuring the geo-mechanical properties of rock retrieved from a well. Many of these techniques are indirect in nature and are typically limited to vertical wells. For example, a variety of physical property measurements that typically correlate with porosity have been used to predict the porosity of a sample or region. Examples include resistivity, sound velocity, gamma-ray back-scattering rates, chargeability (e.g., image logs) and neutron density. X-ray diffraction data may also be used to determine physical properties related to porosity. While such techniques are often useful they do not provide a direct measurement of the desired geo-mechanical property and often require the insertion of equipment into the well. However, with horizontal wells the pressures and temperatures involved and the inaccessibility to horizontal sections of the well typically prohibit the insertion of such equipment. Furthermore, making precise measurements of the geo-mechanical properties of rock (e.g., porosity and brittleness) with many of these techniques requires continued collection of core samples at regular intervals during the drilling process. Unfortunately, core samples currently cannot be effectively extracted from horizontal sections of wells where the geo-mechanical data is most needed.

When core samples are collected, the samples are sent to a laboratory for analysis. In addition to slowing the drilling process to remove the core samples, shipping a large number of core samples to a laboratory may be a costly and time consuming process. For example, getting results from a laboratory and analyzing those results may take weeks or even months before critical decisions about hydrocarbon recovery operations can be made.

Electron microscopy is used in many R&D facilities such as universities, commercial laboratories, and medical research laboratories as a technique for image and spectroscopic analysis. Improvements in hardware and software have allowed these instruments to become more widely used in various industries such as mining and semiconductor manufacturing. Although the increased flexibility, power, and robustness of these systems has enabled their use in a broader range of industries, the ability to gather and process the required quantity of statistically viable data for elemental, mineralogical and textural analysis has been a challenge. Efforts to resolve this challenge have seen the development of hardware and software to handle the spectroscopic aspect of SEM images resulting in wide use in the mining industry.

In contrast to spectroscopy, the use of high resolution back-scatter images of geological samples generated by electron microscopy has been limited to isolating the sample from the suspension media or for the purpose of energy dispersive spectrometry of the sample material. However, data regarding the pore spaces of rock has been neglected in those efforts. This lack of pore-space data has been further highlighted with recent advances in horizontal drilling that make the use of many traditional measures of porosity difficult if not impossible.

Given the foregoing, the ability to timely and accurately determine pore-space metrics for geo-physical samples without inserting measurement equipment into a well and without requiring core samples would advance the art of hydrocarbon exploration and extraction. For example, such metrics could be used to verify the presence of oil shale and determine the geo-mechanical properties thereof as a function of drilling distance. Furthermore, perforations in a well casing could be placed at locations according to the geo-mechanical properties of the surrounding rock resulting in a significant reduction in dry fracturing regions and a corresponding reduction in the cost of recovering hydrocarbon reserves from shale formations and the like.

SUMMARY

As detailed herein, a method for determining pore-space metrics for geological samples may include receiving an image of a geological sample, determining, via image processing, pore-space regions within the image of the geological sample, and measuring the pore-space regions to provide a pore-space metric for the geological sample. The method may also include determining a geo-mechanical property for the geological sample using the pore-space metric and adjusting a hydrocarbon recovery operation according to the pore-space metric or the geo-mechanical property. A corresponding system and apparatus are also disclosed herein.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 3 is a flowchart diagram depicting one embodiment of a measurement and adjustment method for hydrocarbon recovery operations;

FIG. 5 is a dataflow diagram depicting another embodiment of a pore-space image generation apparatus;

FIG. 6a is a table showing one example of results obtained with embodiments disclosed herein;

DETAILED DESCRIPTION

Figure 1:
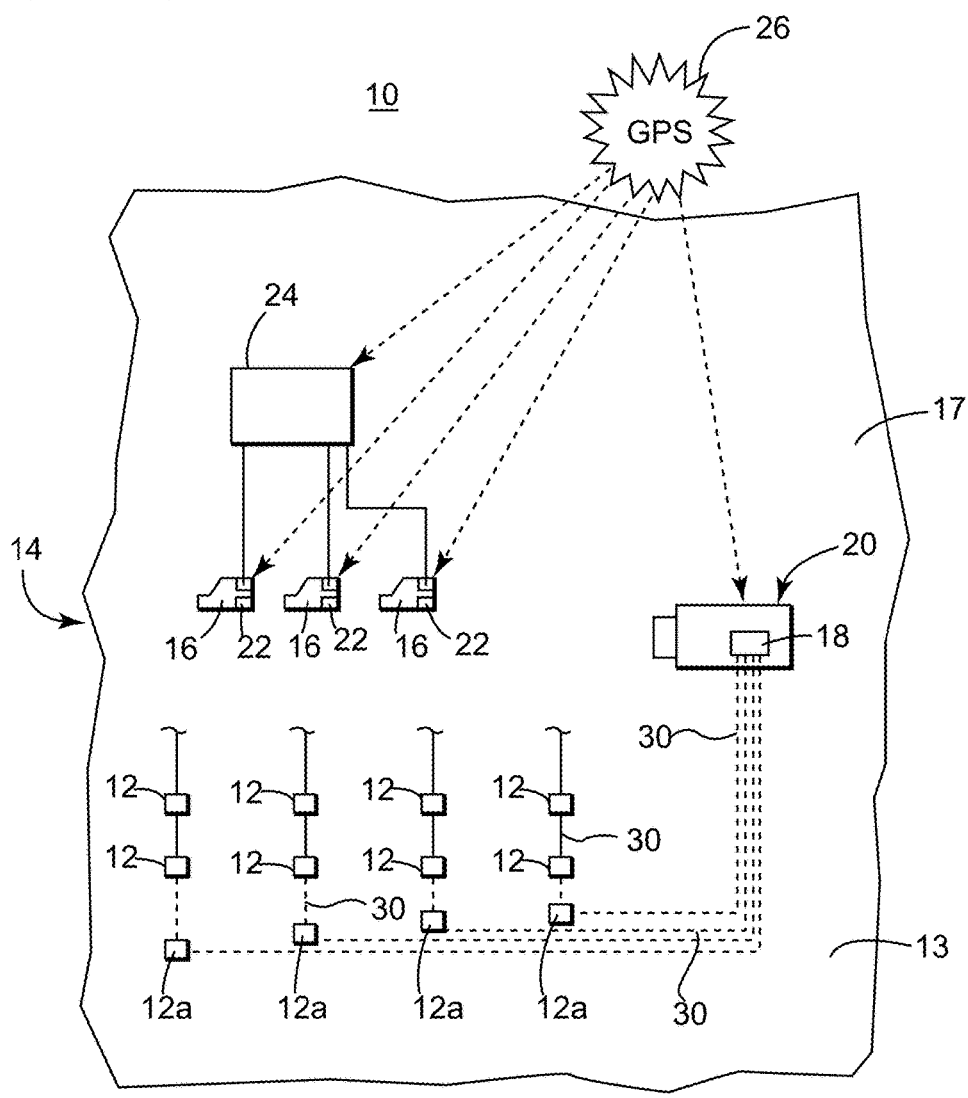
FIG. 1 is a schematic diagram depicting a traditional land seismic survey system used in a prospecting phase for hydrocarbon recovery operations.
Figure 2A:
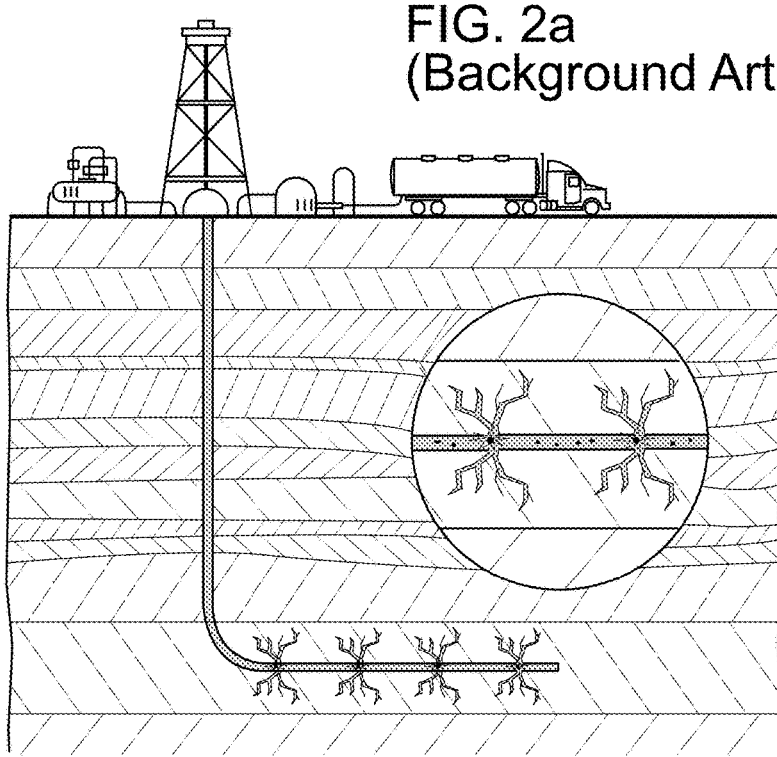
FIGS. 2a and 2b are schematic diagrams depicting the use of fracturing to improve an extraction phase of hydrocarbon recovery operations.
Figure 2B:
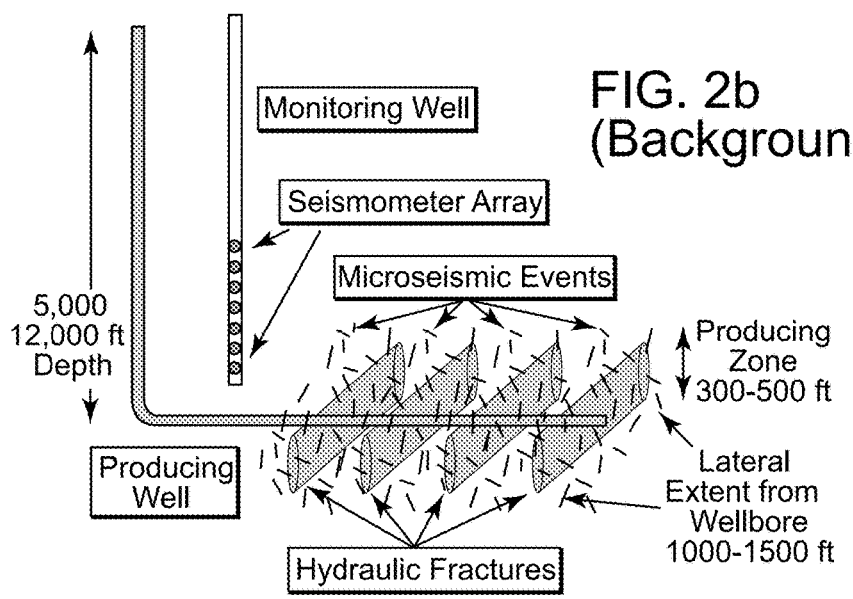

The following description of the exemplary embodiments refers to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures, or characteristics may be combined in any suitable manner in one or more embodiments.

As mentioned in the background section, providing timely and accurate measurements of the geo-mechanical properties of rock can significantly improve both the exploration and extraction phases of hydrocarbon recovery operations. Furthermore, the geo-mechanical properties of rock are highly dependent on the size and distribution of pore spaces which have traditionally not been directly or adequately measured. It is this lack of data on the pore spaces from samples which cannot be easily processed via traditional methods for which the embodiments disclosed herein have been targeted.

Specifically, image processing techniques are leveraged by the embodiments disclosed herein to determine pore-space regions within geological sample images and provide one or more pore-space metrics for the corresponding geological samples. The pore-space metrics can be used to determine one or more geo-mechanical properties for the geological sample and adjust hydrocarbon recovery operations including the exploration and extraction phases of such operations. In some embodiments, the pore-space metrics are used with seismic data to determine the geo-mechanical properties for the geological sample and adjust hydrocarbon recovery operations.

In some embodiments, electron microscopy images of the samples are image-processed to obtain the pore-space metrics for the samples. For example, images generated via scanning electron microscopy or transmission electron microscopy may be image-processed to obtain the pore-space metrics for the samples. Other electromagnetic probing tools such as x-ray tools and optical imaging tools may be used to capture images of samples. The images may be captured at various wavelengths including IR, visible, UV, and X-ray wavelengths. The imaging device and/or an associated illumination device (not shown) that emits bosons or fermions may be used to illuminate the samples for imaging.

FIG. 3 is a flowchart diagram depicting one embodiment of a measurement and adjustment method 300 for hydrocarbon recovery operations. As depicted, the method 300 includes collecting and preparing (310) one or more geological samples, partitioning (320) the geological samples into one or more sampling areas, determining (330) pore-space regions within each sampling area, measuring (340) pore-space metrics, and adjusting (350) a hydrocarbon recovery operation. The method may be conducted in conjunction with finding and extracting hydrocarbons from a known or unknown hydrocarbon reserve.

Collecting and preparing (310) one or more geological samples may include retrieving core extractions and/or cutting remnants and preparing geological samples therefrom in a manner known to those of skill in the art. For example, the extractions and/or remnants may be cut, broken, or crushed to obtain fragments of a suitable size. The suitably sized fragments may then be encased in a suspension media to form samples of a common shape. Examples of suspension media include epoxy, wax, binding powder, plastic, and resin. The commonly shaped samples may also be cut and/or polished to provide a planar face that facilitates imaging and analysis. Preparing the samples may also include treating the samples to cause the pores or grains of the samples to stand out. For example, samples may be treated with a dye such as a fluorescent dye or a non-fluorescent dye that accentuates the pores or the grains.

Partitioning (320) the geological samples into one or more sampling areas may include randomly or methodically selecting areas on the geological sample that are to be imaged and analyzed. The partitioning may be dependent on the imaging and analysis technology used. For example with SEM imaging, which may require considerable time to sequentially scan the entire sample, it may be desirable to select a number of sampling areas that collectively cover a small area compared to the whole sample. However, even with optical imaging, which typically does not require sequential scanning, the time required for analysis (e.g., image processing) may necessitate imaging and analyzing a subset of the entire sample.

Determining (330) pore-space regions within each sampling area may include capturing an image, or a portion of an image, corresponding to each sampling area and conducting image-processing operations to determine the presence and location of pore-space regions within each sampling area. A sample may be illuminated with bosons (e.g. photons) or fermions (e.g. electrons or neutrons) by the imaging device or by illumination equipment associated therewith to facilitate capture of the image.

One or more images that are analyzed to determine the pore-space regions may be captured by measuring fermions or bosons that are emitted from, or passed through, a sample as a result of illumination. For example, electrons or photons that are reflected, diffracted, refracted, fluoresced, transmitted, or otherwise emitted from or passed through a sample may be measured to capture an image of the sample. In certain embodiments, multiple complementary measurement techniques are used to generate one or more images that are used for analysis. For example, complementary spectroscopic data such as energy dispersive X-ray diffraction data and electron diffraction data may be leveraged.

Figure 4A:
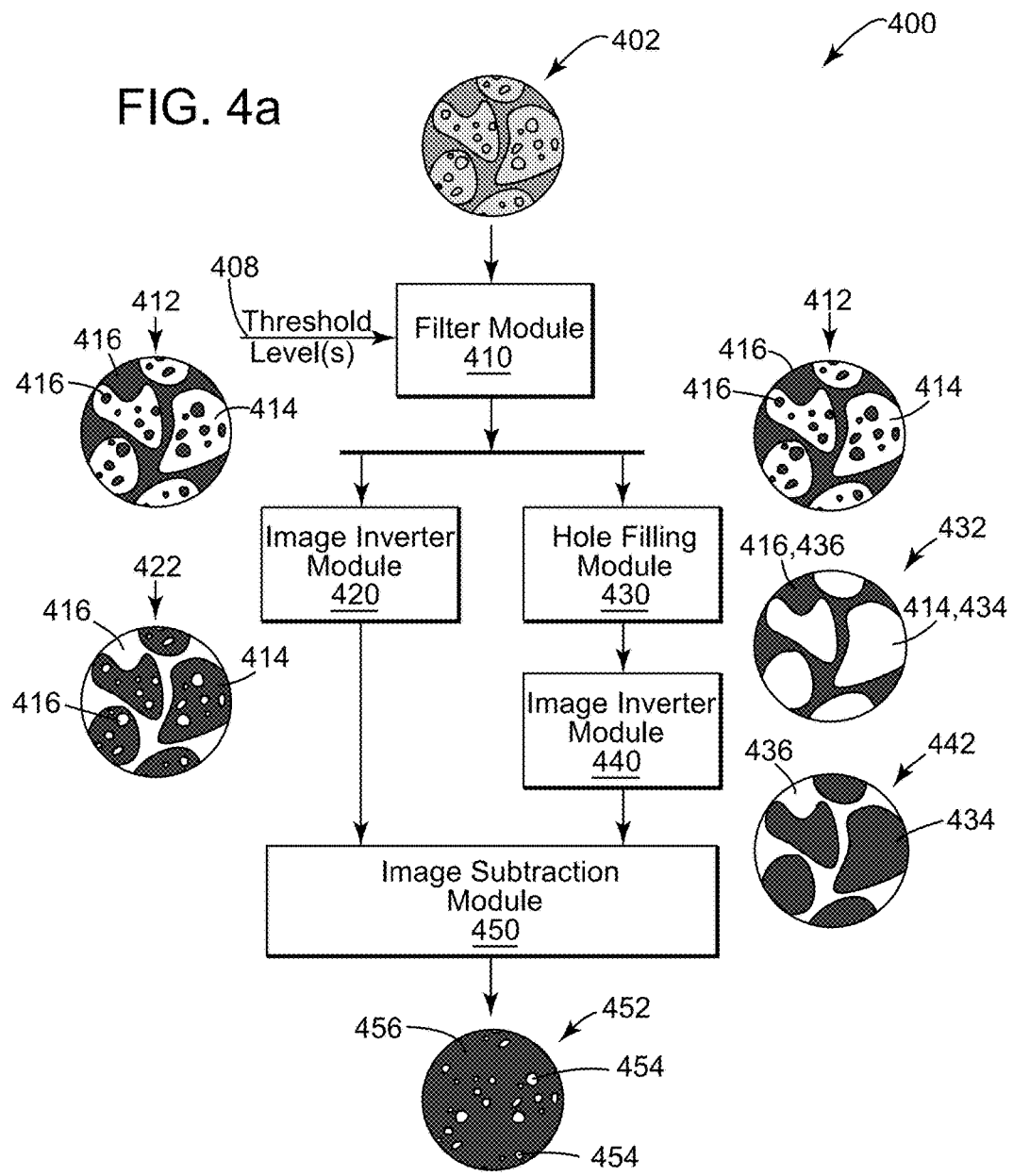
FIG. 4a is a dataflow diagram depicting one embodiment of a pore-space image generation apparatus.

In certain embodiments, mineral and non-mineral regions are determined within each sampling area and non-mineral regions that are completely surrounded (i.e., encompassed) by a single mineral region are determined to be pore-space regions. In some embodiments, the pore-space regions (and other regions used for processing) are formed by clustering pixels of a digital image that meet certain criteria. For more information on determining pore-space regions, and other regions, please see FIGS. 4 and 5 and the associated descriptions.

Measuring (340) pore-space metrics may include conducting a variety of image processing and related operations that provide information about the size and shape of individual pore-space regions. Examples of such information include pore area, circumference, maximum diameter, minimum diameter, and aspect ratio.

Measuring (340) pore-space metrics may also include generating statistics related to the measured parameters such as average, minimum, maximum, mode, and standard deviation values or other distribution related values. The pore-space metrics may also include the overall porosity of a sampling area. In one embodiment, an overall porosity is calculated by dividing the area of the identified pore-space regions by the area of the mineral regions that encompass the pore-space regions (including the pore-space regions).

Adjusting (350) a hydrocarbon recovery operation may include making adjustments that improve the hydrocarbon recovery operation. Examples of improvement include increasing throughput, improving quality, lowering cost, improving safety, and the like. Examples of hydrocarbon recovery operations include prospecting, exploration, conducting seismic surveys, drilling, mining, fracking, pumping, and remediation.

To improve the quality of adjustments made, the pore-space metrics may be used (exclusively or in conjunction with other metrics) to determine or estimate specific geo-mechanical properties for the geological samples. Examples of such properties include a strength property, a brittleness property, a permeability, an organic content saturation, and a water saturation. One of skill in the art may appreciate that pore-space metrics may be readily correlated to various geo-mechanical properties via experimentation, or via published data or formulas such as the brittleness formula of Jarvie et al. See, for example, AAPG Bulletin, v. 91, no. 4 (April 2007), pp. 475-499 which is incorporated herein by reference.

In some embodiments, the pore-space metrics are used with seismic data to determine the geo-mechanical properties for the geological sample and adjust hydrocarbon recovery operations. For example, an inversion workflow process for seismic data (not to be confused with image inversion as discussed herein) may be leveraged along with the pore-space metrics to determine geo-mechanical properties. For more information on inversion workflow and leveraging pore-space metrics see U.S. Provisional Patent Application 61/876,864 entitled "Integration of surface seismic, micro-seismic, mineralogy and rock properties" and U.S. patent application Ser. No. 13/046,447 entitled "Methods and systems for performing azimuthal simultaneous elastic inversion". Each of these references is incorporated herein by reference.

FIG. 4 is a dataflow diagram depicting one embodiment of a pore-space image generation apparatus 400. As depicted, the pore-space image generation apparatus 400 includes a threshold filter module 410, an image inverter module 420, a hole filling module 430, an image inverter module 440, and an image subtraction module 450. The depicted modules may be image processing modules that operate on digital images comprised of pixels.

In some embodiments, the modules depicted in FIG. 4 (and also FIG. 5) are standard image processing modules or functions that are available in open source software programs such as SIP, GIMP, and FIJI, commercial image processing software programs such as Adobe Photoshop® (operating in batch mode) or general technical computing programs such as MATLAB®. In other embodiments, one or more of the modules depicted in FIG. 4 may be custom developed software that executes on a computing device. The images processed by the depicted modules may be digital images comprised of, or convertible to, pixels that have one or more values associated therewith such as intensity, hue, and saturation or similar values common to image processing. For example, the pixels may be greyscale pixels that have intensity values that correspond to back-scattering rates detected by an SEM imaging device.

The threshold filter module 410 may receive a sample image 402 and filter the image according to one or more threshold levels 408 to provide a mineral image 412 comprising mineral (i.e., rock) regions 414 and non-mineral (i.e., non-rock) regions 416. The threshold levels may be selected to distinguish the mineral regions 414 from the non-mineral regions 416. For example, pixels of the sample image 402 with intensity values that exceed a selected threshold may be set by the threshold filter module 410 to a value that indicates that the pixel is a mineral region pixel. Other pixels may be set to a value that indicates that the pixel is a non-mineral region pixel. The pixels may be clustered to form the regions 414 and 416. In the embodiment depicted in FIG. 4, the mineral regions 414 are shown in white and the non-mineral regions 416 (corresponding to void spaces and suspension media regions) are shown in dark gray.

Figure 4B:
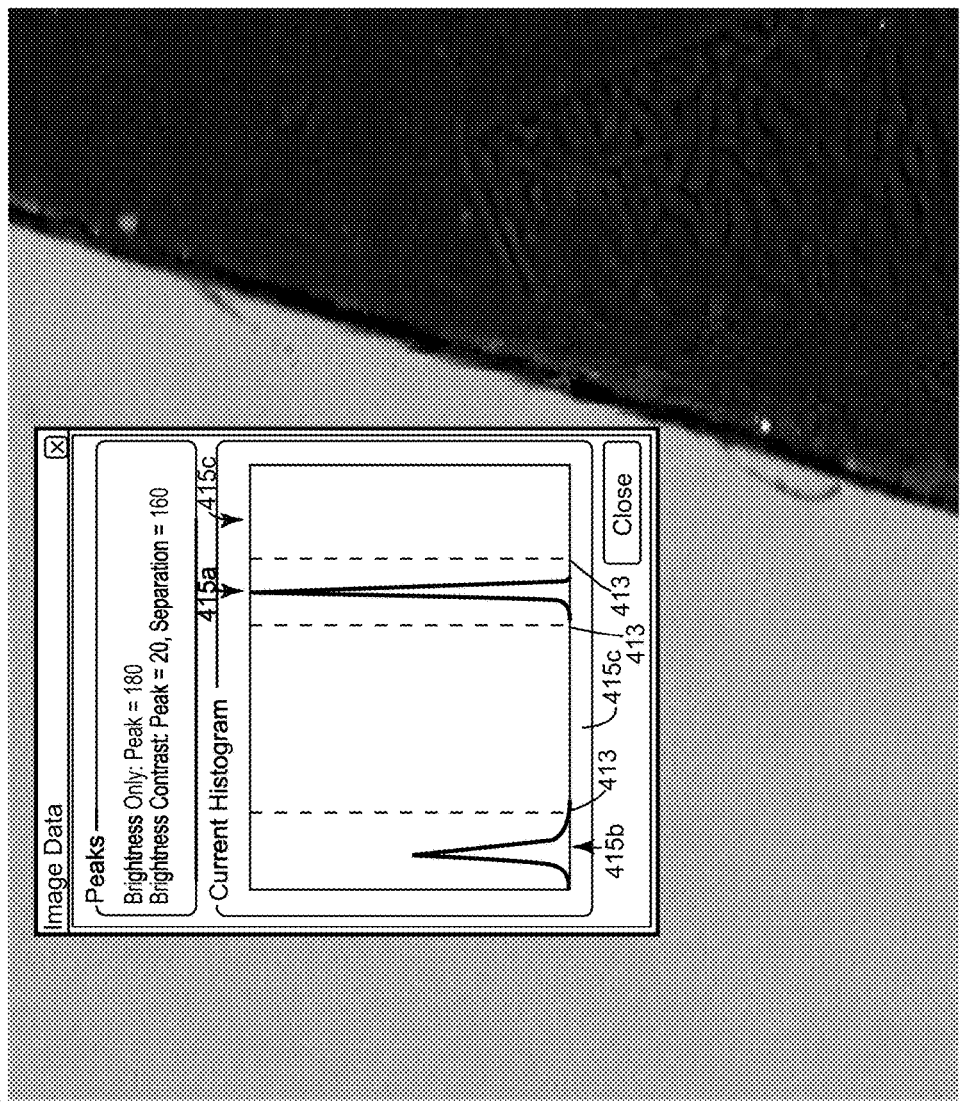
FIG. 4b is a screenshot showing how histogram information can be leveraged to set threshold levels for image processing operations.

In some embodiments, multiple threshold levels 408 are provided and only pixels within a certain range of are assigned to be mineral region pixels by the filter module 410. One of skill in the art will appreciate that potentially noisy images may be processed by providing two or more threshold levels that are used by the threshold filter module 410 to partition the pixel intensity space into a mineral range, a non-mineral range, and one or more undetermined ranges resulting in mineral pixels, non-mineral pixels, and undetermined pixels within the mineral image 412. Consequently, isolated undetermined (i.e., noisy) pixels may be filtered out of the mineral image 412 with additional processing by the filter module 410. For example, FIG. 4b shows how histogram information for a calibration image, or the like, may be used to set multiple threshold levels 413 that partition the pixel intensity space into a mineral range 415a, a non-mineral range 415b, and two undetermined ranges 415c. Consequently, the likelihood of misidentifying a mineral pixel as a non-mineral pixel or vice versa is substantially eliminated.

Returning to FIG. 4a, the image inverter module 420 receives the mineral image 412 and inverts the image to provide a non-mineral image 422 where the non-mineral regions 416 (corresponding to void space and the suspension media) are highlighted. [The reader should be aware that image inversion is a pixel-by-pixel inversion of an image known to those of skill in the art of image processing and that image inversion is different than workflow inversion (mentioned above) which inverts a seismic data matrix through a matrix inversion operation known to those of skill in the art of seismic data processing.] The hole filling module 430 fills non-mineral regions that are completely encompassed by a mineral region to provide a rock region mask 432 comprising rock regions 434 and suspension media regions 436. In one embodiment, the hole filling module 430 scans the mineral image 414 and detects a pixel span corresponding to a hole by detecting a mineral to non-mineral transition followed by a non-mineral to mineral transition. The detected pixel span is then converted to mineral pixels to fill the hole. Subsequently, the filled mineral regions 414 are identified as rock regions 434 and the remaining non-mineral regions 416 are identified as suspension media regions 436.

The image inverter module 430 receives the rock region mask 432 and inverts the image to provide a suspension media mask 442 where the suspension media regions 436 are highlighted. The image subtraction module (alternatively masking module) 450 subtracts the suspension media mask 442 from the non-mineral image 422 to provide the pore-space image 452 comprising pore-space regions 454 and non-pore regions 456. The pore-space image 452 may be used to calculate one or more pore-space metrics for the geological sample capture within the sample image 402.

One of skill in the art will appreciated that the pore-space image may be generated from the sample image with a wide variety of techniques and that the preferred approach may be dependent on the image processing functions (i.e., modules) that are readily available within an image processing library or the like.

FIG. 5 is a dataflow diagram depicting one embodiment of pore-space image generation apparatus 500. As depicted, the pore-space image generation apparatus 500 includes the threshold filter module 410 described above as well as a perimeter filling module 520, and an image inverter module 530. The pore-space image generation apparatus 500 is one example of an alternative embodiment to the pore-space image generation apparatus 400 depicted in FIG. 4.

The perimeter filling module 520 receives the mineral image 412 and provides a negative pore-space image 522 comprising pore-space regions 524 and non-pore regions 526. In one embodiment, the perimeter filling module 520 determines suspension media pixel spans (not shown) within the horizontal scan lines of the image 412 by detecting non-mineral pixels at the edge of the mineral image 412 and advancing into the image until a mineral pixel is detected. The pixels of each suspension media pixel span (not shown) are then assigned to be non-pore region pixels along with all of the pixels within the mineral regions 414. The assigned non-pore region pixels collectively define the non-pore space regions 526. The remaining non-mineral region pixels are assigned to be pore-space pixels that collectively define the pore-space regions 524. The image inverter module 530 inverts the negative pore-space image 522 to provide the (positive) pore-space image 452.

One of skill in the art will appreciate that the functionality provided by the modules of the apparatus 400 and the apparatus 500 may be achieved with a variety of implementations. The functionality may be partitioned in a variety of ways resulting in a variety of modules that collectively provide the described functionality. The pore-space images generated therewith may be used to determine of variety of pore-space metrics and other results for the corresponding geological samples.

Figure 6B:
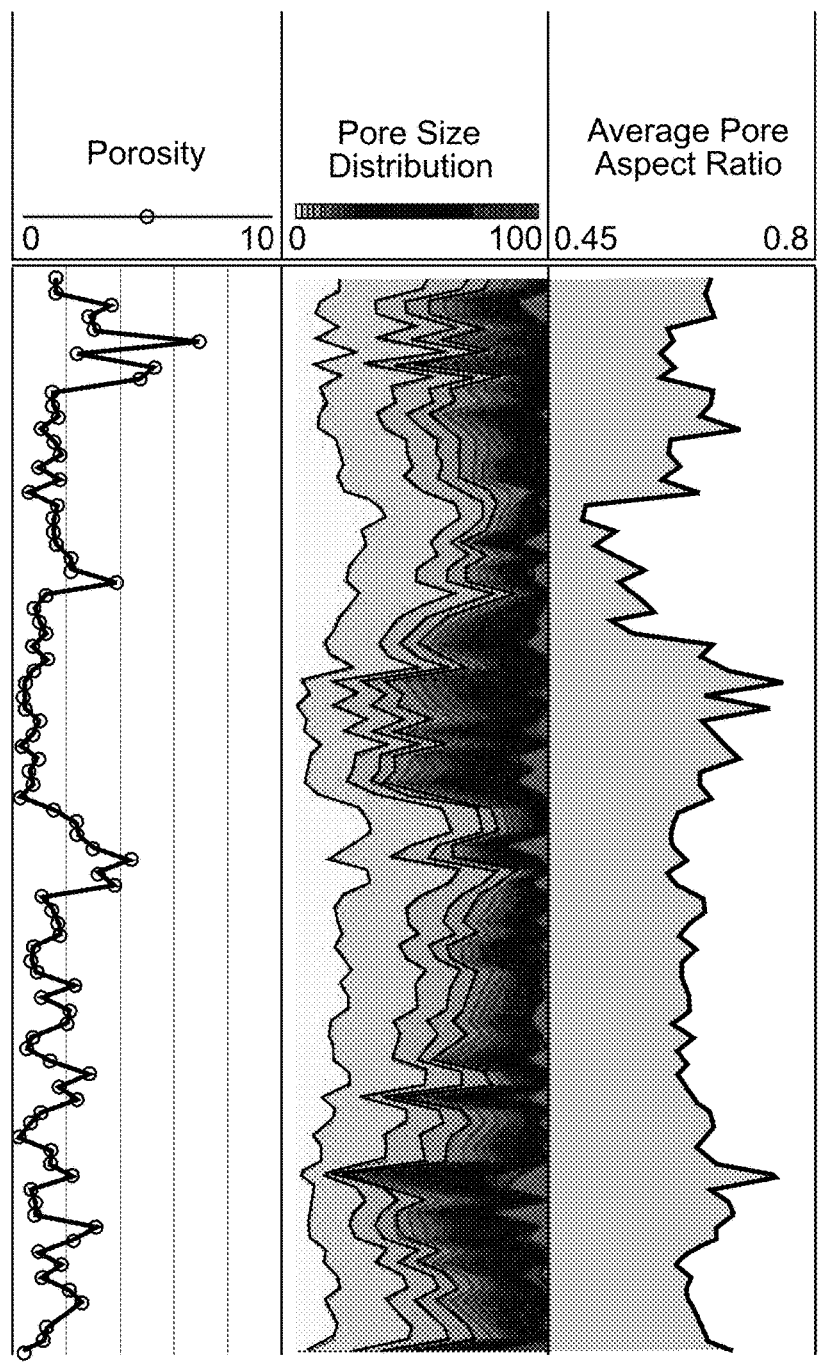
FIG. 6b is a graph showing another example of results obtained with embodiments disclosed herein.

FIG. 6a is a table showing one example of results obtained with embodiments disclosed herein and FIG. 6b is a graph showing another example of results obtained with embodiments disclosed herein. The table in FIG. 6a indicates the maximum and minimum diameter of pores (i.e., the ferret diameter) for each mineral region measured in one geological sample. The graph in FIG. 6b indicates the porosity, pore size distribution, and average pore aspect ratio for each mineral region measured in a geological sample. Much of the information shown in FIGS. 6a and 6b is not directly available with traditional geological measurement techniques.

Figure 6C:
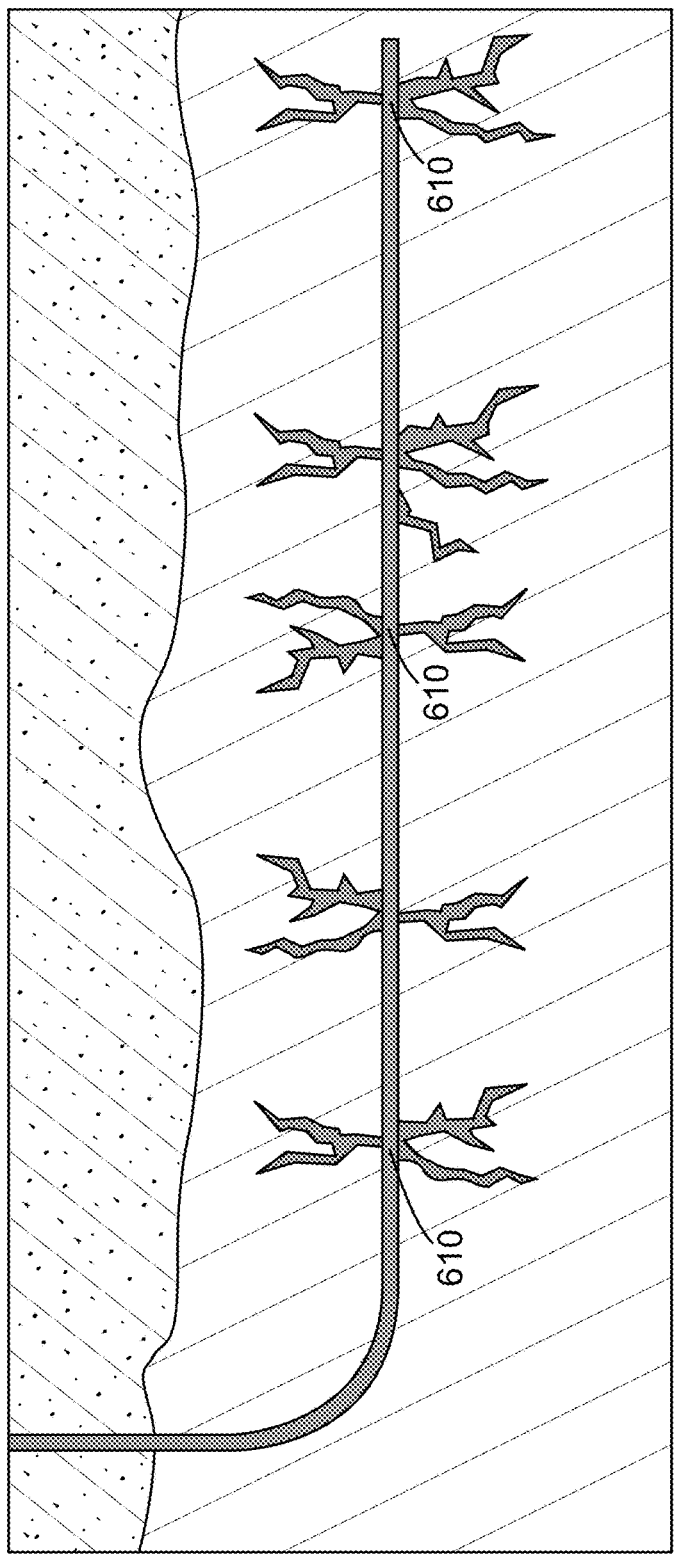
FIG. 6c is a schematic diagram depicting selected placement of fracturing perforations in response to measurements provided by embodiments disclosed herein.

FIG. 6c is a schematic diagram depicting selected placement of fracturing perforations according to the measurements provided by embodiments disclosed herein. Rather than placing the perforations at regular intervals, the perforation locations can be selected based on actual measurements of the rock as a function of position or drilling distance.

The samples that are imaged may be core samples or cutting samples. The use of cutting samples may simplify and speed up the drilling phase of hydrocarbon recovery operations. The images used to measure the pore-space metrics may be SEM images, optical images, or the like. The pore-space metrics measured include a variety of measurements such as pore area, maximum pore diameter, minimum pore diameter, pore aspect ratio, pore circumference, porosity, and pore size distribution.

The images and/or the imaging equipment may be calibrated to provide consistent results. In certain embodiments, one or more image processing parameters such as brightness, contrast, and threshold values (e.g., the threshold levels 408) are manually or automatically adjusted. Calibration samples may be used to facilitate such adjustment. For example, with SEM imaging, one or more calibration samples comprising two or more materials with different average atomic numbers may be used for calibration of the imaging equipment. Examples of such materials could include, but are not limited to, metallic copper, quartz, gold, aluminum, epoxy resin, molybdenum, and manganese.

The SEM equipment may be calibrated so that the total number of electrons hitting the surface of the calibration samples is consistent with a predetermined value. This can be achieved by either direct measurement of the incident electron beam or by measurement of secondary emissions from the incident electron beam. The gain and amplitude of an amplifier associated with the SEM equipment such as an amplifier for a SEM backscatter diode may also be calibrated to obtain standard levels of brightness and contrast. To achieve this, the calibration samples may be used to provide two distinct grey level peaks, as measured by the SEM backscatter diode. The gain and amplitude settings on the backscatter amplifier may also be adjusted such that the distinct atomic weights for the various standard materials in the calibration samples generate predetermined greyscale levels.

When generating images on actual samples, the sample area may be segmented into a grid, and backscatter electron images may be collected from a predetermine number of grid spaces. Each of the collected backscatter electron images may then be processed using a thresholding filter as described above. The threshold value used by the thresholding filter may be set to a predetermined greyscale level that is between the expected greyscale level of the rock being imaged and the suspension media. With optical equipment, similar calibration and segmenting procedures may be used to provide consistent imaging results.

Figure 7:
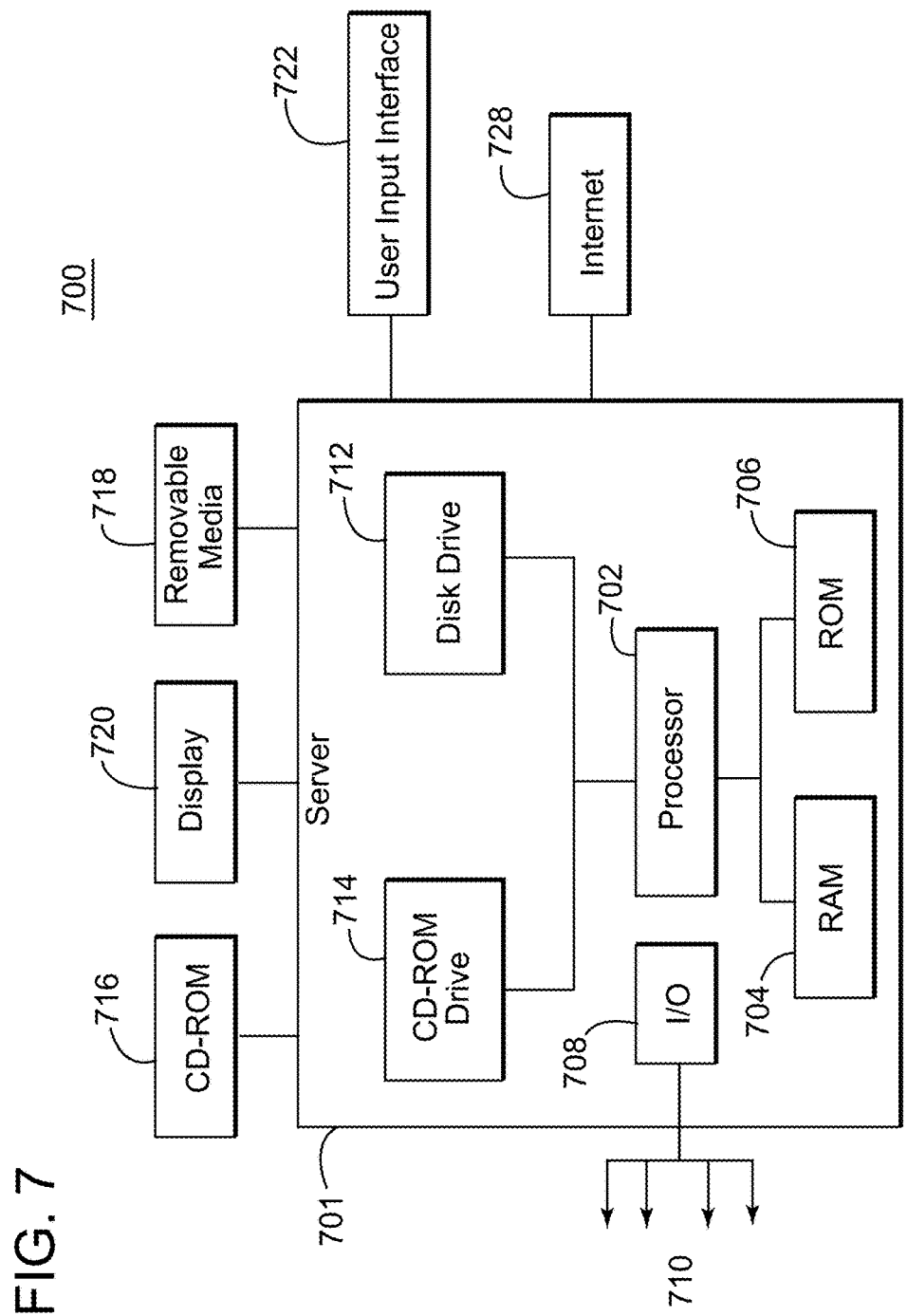
FIG. 7 is a block diagram of a computing device for processing images of geological samples.

The above-discussed procedures and methods may be implemented in a computing device illustrated in FIG. 7. Hardware, firmware, software or a combination thereof may be used to perform the various steps and operations described herein. The computing device 700 of FIG. 7 is one example of a computing structure that may be used in connection with such a system.

The computing device 700 suitable for performing the activities described in the embodiments described herein may include a server 701. Such a server 701 may include a central processor (CPU) 702 coupled to a random access memory (RAM) 704 and to a read only memory (ROM) 706. The ROM 706 may also be other types of storage media to store programs, such as programmable ROM (PROM), erasable PROM (EPROM), etc. The processor 702 may communicate with other internal and external components through input/output (I/O) circuitry 708 and bussing 710, to provide control signals and the like. The processor 702 carries out a variety of functions as are known in the art, as dictated by software and/or firmware instructions.

The server 701 may also include one or more data storage devices, including hard drives 712, CDDROM drives 714, and other hardware capable of reading and/or storing information such as DVD, etc. In one embodiment, software for carrying out the above-discussed steps may be stored and distributed on a CDDROM or DVD 716, a USB storage device 718 or other form of media capable of portably storing information. These storage media may be inserted into, and read by, devices such as the CDDROM drive 714, the disk drive 712, etc. The server 701 may be coupled to a display 720, which may be any type of known display or presentation screen, such as LCD displays, plasma display, cathode ray tubes (CRT), etc. A user input interface 722 is provided, including one or more user interface mechanisms such as a mouse, keyboard, microphone, touchpad, touch screen, voice-recognition system, etc.

The server 701 may be coupled to other devices, such as sources, detectors, etc. The server may be part of a larger network configuration as in a global area network (GAN) such as the Internet 728, which allows ultimate connection to the various landline and/or mobile computing devices.

In summary, the methods, apparatuses, and systems presented herein provide a number of distinct advantages over prior art methods, apparatuses, and systems. It should be noted that many of the functional units described herein such as those related to image processing are identified as modules. Others are assumed to be modules. One of skill in the art will appreciate that the various modules described herein may include a variety of hardware components that provide the described functionality including one or more processors such as CPUs or microcontrollers that are configured by one or more software components. The software components may include executable instructions or codes and corresponding data that are stored in a storage medium such as a non-volatile memory, or the like. The instructions or codes may include machine codes that are configured to be executed directly by the processor. Alternatively, the instructions or codes may be configured to be executed by an interpreter, or the like, that translates the instructions or codes to machine codes that are executed by the processor.

It should also be understood that this description is not intended to limit the invention. On the contrary, the exemplary embodiments are intended to cover alternatives, modifications, and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method comprising:
receiving an image of a geological sample, wherein the image is obtained by microscopy;
determining, via image processing, pore-space regions and non-pore regions within the image of the geological sample; and
measuring the pore-space regions within the image of the geological sample to provide a pore-space metric for the geological sample,
wherein image processing comprises filtering the image with a threshold filter, inverting the filtered image and subtracting the inverted image from the filtered image to yield a result image, which is then used for the measuring.

2. The method of claim 1, further comprising determining a geo-mechanical property for the geological sample using the pore-space metric.

3. The method of claim 2, wherein the geo-mechanical property is a strength property or a brittleness property.

4. The method of claim 3, further comprising adjusting a hydrocarbon recovery operation according to the geo-mechanical property.

5. The method of claim 1, wherein image processing comprises conducting a fill operation including at least one of hole filling and perimeter filling.

6. The method of claim 1, wherein image processing comprises determining mineral regions for the geological sample.

7. The method of claim 1, wherein image processing comprises determining suspension media regions for the geological sample.

8. The method of claim 1, further comprising adjusting a hydrocarbon recovery operation according to the pore-space metric.

9. The method of claim 1, further comprising partitioning the geological sample into a plurality of sampling regions and measuring the pore-space metric for each sampling region.

10. The method of claim 1, wherein the image of the geological sample is generated by electron microscopy.

11. The method of claim 1, wherein the image of the geological sample is generated by optical microscopy.

12. A system comprising:
a computing device configured to determine pore-space metrics for geological samples, the computing device comprising
an interface configured to receive an image of a geological sample, the image being obtained by microscopy, and a processor configured to determine, via image processing, pore-space regions and non-pore regions within the image of the geological sample, and to measure the pore-space regions within the image of the geological sample to provide a pore-space metric for the geological sample, wherein image processing comprises filtering the image with a threshold filter, inverting the filtered image and subtracting the inverted image from the filtered image to yield a result image, which is then used for the measuring.

13. The system of claim 12, further comprising a microscope configured to capture the image of the geological sample.

14. The system of claim 13, wherein the microscope or an associated device illuminates the geological sample with electrons.

15. The system of claim 13, wherein the microscope or an associated device illuminates the geological sample with photons.

16. The system of claim 12, wherein the processor is further configured to determine a geo-mechanical property for the geological sample using the pore-space metric.

17. The system of claim 12, wherein the processor is further configured to adjust a hydrocarbon recovery operation according to the pore-space metric.

18. The system of claim 17, further comprising hydrocarbon recovery equipment.

19. A method comprising:

receiving an image of a geological sample, wherein the image is obtained by microscopy;

filtering the image using at least one threshold to identify mineral regions within the filtered image;

determining, via image processing, pore-space regions, non-pore regions and/or suspension media regions within the image of the geological sample;

measuring the pore-space regions within the image of the geological sample to provide a pore-space metric for the geological sample;

determining a geo-mechanical property for the geological sample using the pore-space metric; and adjusting a hydrocarbon recovery operation according to the geo-mechanical property, wherein image processing comprises filtering the image with a threshold filter, inverting the filtered image and subtracting the inverted image from the filtered image to yield a result image, which is then used for the measuring.

* * * * *